United States Patent [19]

Jakob et al.

[11] Patent Number: 4,914,208
[45] Date of Patent: Apr. 3, 1990

[54] OPTICALLY ACTIVE SALTS OF A SUBSTITUTED THIAZOLIDINE-4-CARBOXYLATE AND 3-CHLORO-2-HYDROXYPROPYL-TRIMETHYL AMMONIUM, THEIR PREPARATION AND USE

[75] Inventors: Harald Jakob, Hasselroth; Klaus Huthmacher, Gelnhausen; Herbert Klenk, Hanau; Axel Kleemann, Muehlheim; Gunes Giray, Kleinostheim, all of Fed. Rep. of Germany

[73] Assignee: Degussa Aktiengesellschaft, Frankfurt, Fed. Rep. of Germany

[21] Appl. No.: 262,722

[22] Filed: Oct. 17, 1988

[30] Foreign Application Priority Data

Oct. 22, 1987 [DE] Fed. Rep. of Germany ....... 3735757

[51] Int. Cl.$^4$ .......................................... C07D 277/06
[52] U.S. Cl. .................................................... 548/201
[58] Field of Search ........................................ 548/201

[56] References Cited

FOREIGN PATENT DOCUMENTS 160269 7/1987 Japan .................................... 548/201

*Primary Examiner*—Robert Gerstl
*Attorney, Agent, or Firm*—Beveridge, DeGrandi & Weilacher

[57] ABSTRACT

The invention relates to the preparation of optically active salts of the general formula

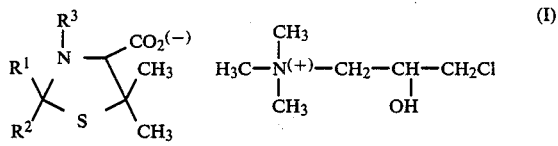

from which the corresponding optically active 3-chloro-2-hydroxypropyltrimethyl ammonium chloride can be obtained by treatment with mineral acid.

The L(−) form of this compound is a valuable component for the synthesis of L(−) carnitine.

3 Claims, No Drawings

OPTICALLY ACTIVE SALTS OF A SUBSTITUTED THIAZOLIDINE-4-CARBOXYLATE AND 3-CHLORO-2-HYDROXYPROPYLTRIMETHYL AMMONIUM, THEIR PREPARATION AND USE

This invention relates to new, optically active salts of a substituted thiazolidine-4-carboxylate and 3-chloro-2-hydroxypropyltrimethyl ammonium and their use for preparing an optically active 3-chloro-2-hydroxypropyltrimethyl ammonium chloride (Quab ®188). The L-(—) compound is a valuable component for the synthesis of L-(—) carnitine. The preparation of L-(—) carnitine had been effected by resolution of racemates of the appropriate precursors, carnitine nitrile chloride and carnitine amide chloride. This method required that initially the chloride ion had to be removed with silver salts (DD-PS 23 217), anion exchangers (DE-OS 2 927 672) or electrodialysis (DE-OS 3 342 713) and replaced by an optically active carboxylate.

These methods resulted in the accumulation of large amounts of salt impurities which are difficult to separate and make the resolution of racemates more difficult but there also resulted the accumulation of the D-enantiomer, which is not racemizable and therefore cannot be reused. The buildup of these substances caused problems of an ecological nature.

It has been found that by resolution of racemates of an early precursor, that is, of Quab ®188, the subsequent steps in the synthesis to L-carnitine are free of the undesired enantiomeric compounds. This is of great significance for an economically sound synthesis. In addition, the D-(+)-Quab enantiomer, which is not useful for the synthesis of L-carnitine has other uses known for Quab.

EP-A-0157315 teaches a method of preparing optically active di-(3-chloro-2-hydroxypropyltrimethyl ammonium)-tartrate from which the desired compound can be obtained by removal of the tartrate.

However, tartaric acid is not a desirable reagent for industrial purposes because its high water solubility makes its recovery from the aqueous solutions obtained at the release of Quab 188 from the corresponding salt pair highly uneconomical. Moreover, the yield of released, optically active Quab is not satisfactory on account of the slight difference in solubility of Quab 188 and tartaric acid in water in organic solvents.

This invention is directed to breaking down Quab 188 into its optical antipodes in a manner which is simpler and more economical than heretofore.

The subject matter of the invention is optically active salts of the general formula:

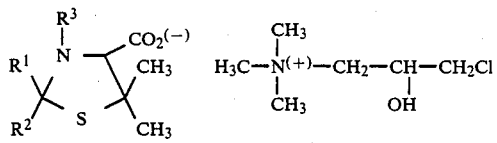

wherein
R$^1$ and R$^2$ each are independently hydrogen, alkyl of 1 to 8 carbon atoms, cycloalkyl of 4 to 11 carbon atoms, with the proviso that only one of R$^1$ or R$^2$ may be cycloalkyl;
R$^3$ is an acyl group selected from benzoyl, tosyl, nitrophenyl sulfenyl, acetyl or formyl.

Compounds wherein R$^1$ and R$^2$ are methyl and ethyl are preferred.

The following are preferred embodiments: The salt of D-(+)-3-formyl-2,2,5,5-tetramethyl thiazolidine-4-carboxylate and L-(—)-3-chloro-2-hydroxypropyltrimethyl ammonium and the salt of L-(—)-3-formyl-2,2,5,5-tetramethyl thiazolidine-4-carboxylate and D-(+)-3-chloro-2-hydroxypropyltrimethyl ammonium.

A method for preparing the optically active salts of the general formula (I) is characterized in that racemic epichlorohydrin is reacted with the trimethyl ammonium salt of an optically active acid of the general formula:

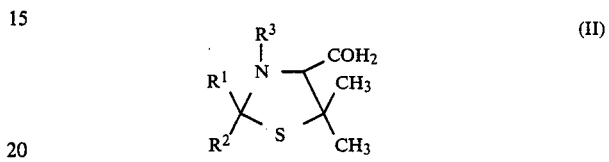

in which R$^1$, R$^2$, R$^3$ have the meanings indicated above. The optically pure thiazolidine-4-carboxylic acids of the general formula (II) can be obtained in a known manner, e.g. using brucine (GB-PS 585-413), but preferably using 1-phenylpropanolamine (DE-OS 2 138 121), from the racemic acid mixtures.

A preferred method of preparing the optically active salts of general formula (II) is characterized in that 0.9 to 1.2 moles trimethylamine per mole of the optically active acid is added at 0° to 30° C. to an optically active acid of the general formula (II) suspended in water or dissolved in an organic solvent.

It is also possible to proceed in the inverse manner in that the solution of trimethylamine in water or preferably in an organic solvent is mixed with the acid of general formula (II). The trimethyl ammonium thiazolidine-4-carboxylate formed as intermediate product is subsequently converted with epichlorohydrin at temperatures of 5° to 30° C. into the desired salt pair and its diastereomer.

A particular advantage of the method of the invention resides in the fact that the salts of the particular diastereomeric salt pairs exhibit considerable differences in solubility in organic solvents and therefore permit an easy separation into crystallizate and mother liquor. According to the previous observations, the salts of D-acid (I) with the L-(—)-Quab are more difficulty or even substantially more difficulty soluble than the diastereomeric D,D salts; the same naturally applies to the relationship of the L,D salts to the L,L salts.

If the reaction is carried out in water, the water must be evaporated subsequently and the residue recrystallized by treatment with an organic solvent. In order to increase the optical purity, the separated salt pair can be washed, advantageously with acetone, or also recrystallized as usual, e.g. from alcohol.

A preferred embodiment for preparing the D,L salt pair consists in adding to 1 mole of the substituted D-(+)-thiazolidine-4-carboxylic acid, suspended in water or in lower alcohols or mixtures of alcohol/acetone, alcohol/methylene chloride or alcohol/ethyl acetate, 0.9 to 1.2 moles trimethyl amine, preferably 1.0 to 1.1 mole trimethyl amine, at temperatures of 0° to 30° C. The reaction mixture is treated in a pH range of 7-9 with 0.8 to 1.2 moles epichlorohydrin and the temperature is maintained at 5°-30° C., preferably at 15° to 20° C.

The release of the optically active Quab 188 from the salt can take place in a customary manner, in which instance the method of the invention offers the special engineering advantage that the optically active acids according to general formula (II) are slightly water-soluble and can therefore be recovered in high yields without any distillation and extraction expense.

For example, a solution of the salt pair in water can be mixed with a strong mineral acid such as hydrochloric acid, the precipitated optically active split acid separated and returned after drying to the resolution of racemates. In order to obtain the optically active Quab 188 accumulating in a high yield in a high degree of purity, the aqueous solution is washed with an organic solvent immiscible with water such as methylene chloride and the optically active Quab 188 is isolated by evaporating the water or is used as an aqueous solution for carnitine synthesis.

The procedure can also be carried out by changing the solvent, that is, a suspension of salt pair and organic solvent such as acetone or isopropanol, is mixed with hydrochloric acid and the insoluble, optically active Quab 188 isolated by separation. After concentration by evaporation of the organic solvent, the optically active split acids are recovered in high yields. This is the preferred method for use in the recovery of the optically active split acid from the mother liquor of the salt pair formation.

Data: D,L salt pair

Empirical formula: $C_{15}H_{29}ClNO_4S$
Molecular weight: 368.92
Elementary analysis: calcd.: C 48.85, H 7.87, Cl 9.63, N 7.60. found: C 49.07, H 8.01, Cl 9.72, N 7.82.
Melting point: 151° C. (after recrystallization from isopropanol)
$[\alpha]_D^{20} = +31.4°$ (c=1, $H_2O$)

EXAMPLES

Example 1

119 ml of a 4.2 m (0.5 mole) trimethyl amine solution in ethanol was added dropwise at room temperature within 45 minutes to a suspension of 108.6 g (0.5 mole) D-(+)-3-formyl-2,2,5,5-tetramethyl-thiazolidine-4-carboxylic acid in 240 ml acetone. The temperature rose thereby from 20° to 26° C. and a clear solution was produced. It was agitated 20 minutes more and subsequently 39.2 ml (0.5 mole) epichlorohydrin was added dropwise during 20 minutes at 25° C. The reaction mixture was agitated 48 hours at this temperature, then cooled to 5° C. and the salt of L-(−)-3-chloro-2-hydroxypropyltrimethyl ammonium and D-(+)-3-formyl-2,2,5,5-tetramethyl thiazolidine-4-carboxylic acid removed by suction. After washing with acetone and drying in a vacuum, 51.0 g (27.6%) salt pair were obtained.
$[\alpha]_D^{20} = +31.5°$ (c=1, $H_2O$)
Melting point: 150° to 151° C.

Example 2

108.6 g (0.5 mole) D-(+)-3-formyl-2,2,5,5-tetramethyl thiazolidine-4-carboxylic acid were suspended in a mixture of 70 ml ethanol and 200 ml ethyl acetate under agitation and 32.3 g (0.55 mole) trimethyl amine was introduced during 40 minutes at 15°-20° C. The clear solution was mixed with 39.2 ml (0.5 mole) epichlorohydrin and agitated 2 days at 25° C. The precipitated salt pair was filtered off by suction, washed with 150 ml acetone and dried in a vacuum: 76.12 g (41.3%). $[\alpha]_D^{20} = +31.8°$ (c=1, $H_2O$) Melting point: 146° to 147° C.

Example 3

34.8 g (0.59 mole) trimethyl amine was mixed at 15° C. with 200 ml ethyl acetate and 70 ml ethanol, heated to 5° C. and 129.0 g (0.59 mole) D-(+)-3-formyl-2,2,5,5-tetramethyl thiazolidine-4-carboxylic acid was added in portions. The reaction mixture was slowly heated to room temperature and 46.3 ml (0.59 mole) epichlorohydrin was added dropwise. The reaction mixture was agitated 4 days at 25° C., the precipitate that formed was filtered with suction, washed and dried. 76.06 g (34.7%) salt pair. $[\alpha]_D^{20} = +31.4°$ (c=1, $H_2O$) Melting point: 150° C.

Example 4

217.3 g (1.0 mole) D-(+)-3-formyl-2,2,5,5-tetramethyl thiazolidine-4-carboxylic acid, 65.0 g (1.1 mole) trimethyl amine and 70.4 ml (0.9 mole) epichlorohydrin were reacted in 500 ml isopropanol as described in example 2. The reaction mixture was agitated at an internal temperature of 15° C. for a total of 2 days. The precipitated crystal pulp was removed by suction, washed with a total of 250 ml acetone and dried: 136.0 g (41%) salt pair. $[\alpha]_D^{20} = +32.9°$ (c=1, $H_2O$)

For further purification, the solid was suspended in 500 ml acetone and heated under vigorous agitation for 0.5 hours to reflux. After cooling, removal by suction and drying in a vacuum, 131.0 g (39.5%) salt pair were obtained. $[\alpha]_D^{20} = +32.0°$ (c=1, $H_2O$) Melting point: 149°-150° C.

Example 5

217.3 g (1.0 mole) D-(+)-3-formyl-2,2,5,5-tetramethyl thiazolidine-4-carboxylic acid, 65.0 g (1.1 mole) trimethyl amine and 78.4 ml (1.0 mole) epichlorohydrin were reacted in 600 ml acetone, as described in example 2. After removal of the solid by suction at room temperature, 154.5 g (41.9%) salt pair were obtained. $[\alpha]_D^{20} = +34.6°$ (c=1, $H_2O$) Melting point: 135° to 137° C.

Example 6

Preparation of L-(−)-3-chloro-2-hydroxypropyltrimethyl ammonium chloride [L-(−)-Quab 188]

31 ml 36% hydrochloric acid were added dropwise within 30 minutes at 10° C. to a solution of 130.1 g (0.353 mole) salt pair. $[\alpha]_D^{20} = +32.0°$, (c=1, $H_2O$) in 300 ml water. The reaction mixture was agitated 30 minutes more at this temperature (pH of the suspension: 2.0). The precipitated D-(+)-3-formyl-2,2,5,5-tetramethyl thiazolidine-4-carboxylic acid was removed by suction, washed with 100 ml water and dried at 60° C. in a vacuum. There were obtained 72.3 g (94.3%). The aqueous filtrate was extracted twice with 100 ml methylene chloride. After separation and concentration by evaporation of the organic phase as well as drying of the residue, another 2.0 g were recovered, thus making a total of 74.3 g (97.0%) D-(+)-3-formyl-2,2,5,5-tetramethyl thiazolidine-4-carboxylic acid ($[\alpha]_D^{20}+52.0°$; c=1, ethanol).

The aqueous phase was concentrated in a vacuum at 45° C. bath temperature to dryness and was treated twice with 100 ml acetone each time and again concentrated. The remaining residue was digested with 150 ml acetone, removed by suction and dried in a vacuum at 40° C. There were obtained 65.1 g (98%) L-(−)-Quab 188 as colorless crystals. $[\alpha]_D^{20} = -28.7°$ (c=1, H$_2$O) Melting point 213° to 214° C.

After renewed digesting with acetone, the amount of rotation was $[\alpha]_D^{20} = -29.9°$ (c=1, H$_2$O).

Example 7

Preparation of L-(−)-3-chloro-2-hydroxypropyl-trimethyl ammonium chloride [L-(−)-Quab 188]

A suspension of 360.0 g (0.976 mole) salt pair $[\alpha]_D^{20} = +32.6°$, (c=1, H$_2$O) in 1.7 liters acetone was cooled to 5° C. and treated for 45 minutes successively with 45.3 g 36% (0.46 mole) and 19.0 g (0.52 mole) gaseous hydrochloric acid.

The reaction mixture was then agitated 30 minutes more at 5° C. The precipitated product was removed by suction, washed with 100 ml acetone and dried at 40° C. in a vacuum: 176.0 g (95.9%) L-(−)-Quab 188. $[\alpha]_D^{20} = -28.5°$ Melting point: 214° to 215° C. The filtrate was concentrated by evaporation in a rotary evaporator, the residue was mixed with 300 ml water and partially condensed by evaporation. The suspension obtained in this manner was filtered by suction and rewashed with 100 ml water. After drying, there were obtained 207.4 g (97.8%) D-(+)-3-formyl-2,2,5,5-tetramethyl thiazolidine-4-carboxylic acid. Extraction of the aqueous filtrate with methylene chloride yielded an additional 3.9 g and thus a total of 211.3 g (99.6%) optically active split acid were obtained.

German priority application P 37 35 757.3 is incorporated herein by reference.

We claim:

1. Optically active salt of the general formula

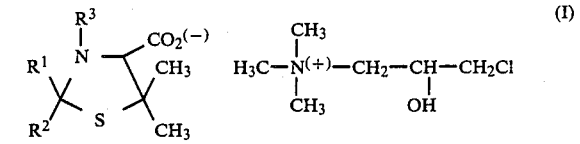

wherein

R$^1$ and R$^2$ each are independently hydrogen, alkyl containing carbon atoms 1 to 8 carbon atoms, or cycloalkyl of 4 to 11 carbon atoms with the proviso that only one of R$^1$ or R$^2$ maybe cycloalkyl, R$^3$ is an acyl group selected from benzoyl, tosyl, nitrophenyl sulfenyl, acetyl or formyl.

2. An optically active salt of the formula D-(+)-3-formyl-2,2,5,5-tetramethylthiazolidine-4-carboxylate and L-(−)-3-chloro-2-hydroxypropyltrimethyl ammonium.

3. An optically active salt of the formula L-(−)-3-formyl-2,2,5,5-tetramethylthiazolidine-4-carboxylate and D-(+)-3-chloro-2-hydroxypropyltrimethyl ammonium.

* * * * *